US009717633B2

(12) United States Patent
Waters et al.

(10) Patent No.: US 9,717,633 B2
(45) Date of Patent: Aug. 1, 2017

(54) LIGHTED HEADGEAR

(71) Applicants: Michael Waters, Aspen, CO (US); Charles Waters, Aspen, CO (US)

(72) Inventors: Michael Waters, Aspen, CO (US); Charles Waters, Aspen, CO (US)

(*) Notice: Subject to any disclaimer, the term of this patent is extended or adjusted under 35 U.S.C. 154(b) by 298 days.

(21) Appl. No.: 14/212,738

(22) Filed: Mar. 14, 2014

(65) Prior Publication Data

US 2014/0259287 A1    Sep. 18, 2014

Related U.S. Application Data

(60) Provisional application No. 61/794,017, filed on Mar. 15, 2013.

(51) Int. Cl.

| H04R 5/033 | (2006.01) |
| F21V 21/084 | (2006.01) |
| A61F 11/14 | (2006.01) |
| A41D 13/00 | (2006.01) |
| F21V 33/00 | (2006.01) |
| F21L 4/02 | (2006.01) |
| H04R 5/00 | (2006.01) |
| F21V 21/00 | (2006.01) |
| F21Y 115/10 | (2016.01) |

(52) U.S. Cl.
CPC .......... *A61F 11/14* (2013.01); *A41D 13/0002* (2013.01); *F21L 4/02* (2013.01); *F21V 33/0004* (2013.01); *F21V 33/0056* (2013.01); *F21Y 2115/10* (2016.08)

(58) Field of Classification Search
CPC .. F21V 21/084; F21V 21/088; F21V 21/0885; F21V 21/096; F21V 21/0965

USPC ........ 381/371, 370, 384; 362/105, 106, 103; 181/129
See application file for complete search history.

(56) References Cited

U.S. PATENT DOCUMENTS

| 645,984 A | 3/1900 | Tournier |
| 909,742 A | 1/1909 | Borchert |
| 1,098,628 A | 6/1914 | Hyman |

(Continued)

FOREIGN PATENT DOCUMENTS

| AU | 1178576 | 9/1977 |
| AU | 6310994 | 11/1994 |

(Continued)

OTHER PUBLICATIONS

'Panther Vision Power Beanie—Available at Bunnings Warehouse,' screenshot of a video posted to Youtube on Jun. 16, 2014. Retrieved from the Internet on Mar. 9, 2015. URL: https://www.youtube.com/watch?v=ZOWodRoEuvc. (1 page).

(Continued)

*Primary Examiner* — Edgardo San Martin
(74) *Attorney, Agent, or Firm* — Fitch, Even, Tabin & Flammery LLP

(57) ABSTRACT

Lighted headgear, and more particularly lighted earwear such as earmuffs or headphones, is provided herein that are configured to mount or secure to a user's head while providing light forwardly thereof. The lighted headgear includes ear engaging or covering assemblies, which can be connected by a headband or other crown portion. The ear covering assemblies can include one or more light sources mounted thereto or can have a light module secured thereto to provide a user with hands-free lighting.

29 Claims, 4 Drawing Sheets

(56) References Cited

U.S. PATENT DOCUMENTS

| | | |
|---|---|---|
| 1,109,415 A | 9/1914 | Harris |
| 1,261,824 A | 1/1918 | La Vine |
| 1,255,265 A | 2/1918 | Zachara |
| 1,323,822 A | 12/1919 | Bramming |
| D58,302 S | 7/1921 | Bartholomew |
| 1,438,586 A | 12/1922 | Eaton |
| 1,448,353 A | 3/1923 | Barany |
| 1,475,653 A | 11/1923 | Rosenberg |
| 1,572,210 A | 2/1926 | Kolibas |
| 1,615,067 A | 1/1927 | Boerman |
| 1,744,777 A | 1/1930 | Lundgren |
| 1,749,998 A | 3/1930 | Collins |
| 1,879,512 A | 9/1932 | Rotea |
| 1,883,756 A | 10/1932 | Bloom |
| D114,980 S | 1/1939 | Wengen |
| 2,196,543 A | 4/1940 | Anderson |
| 2,373,553 A | 10/1942 | Fetterman |
| D137,375 S | 2/1944 | Heit |
| 2,369,829 A | 2/1945 | Johnson |
| 2,461,254 A | 2/1949 | Bassett |
| 2,473,394 A | 6/1949 | Scott |
| 2,531,585 A | 11/1950 | Pope |
| 2,540,435 A | 2/1951 | Ferguson |
| 2,552,764 A | 5/1951 | Bedford, Jr. |
| 2,567,046 A | 9/1951 | Anderson |
| 2,591,112 A | 4/1952 | Zwierzynski |
| 2,638,532 A | 5/1953 | Brady |
| 2,640,980 A | 6/1953 | Prupis |
| 2,705,751 A | 4/1955 | Harris |
| 2,730,720 A | 1/1956 | Saunders |
| 2,788,439 A | 4/1957 | Hesse |
| 2,904,670 A | 9/1959 | Calmes |
| 2,966,580 A | 12/1960 | Taylor |
| 2,978,696 A | 4/1961 | Keller |
| 3,008,040 A | 11/1961 | Moore |
| 3,032,647 A | 5/1962 | Wansky |
| 3,040,881 A | 6/1962 | McNeill |
| 3,057,992 A | 10/1962 | Baker |
| 3,060,308 A | 10/1962 | Fortuna |
| 3,123,208 A | 3/1964 | Barnum |
| 3,184,058 A | 5/1965 | Crowther |
| 3,201,771 A | 8/1965 | Proulx |
| D207,919 S | 6/1967 | Fai |
| 3,350,552 A | 10/1967 | Lawrence |
| 3,358,137 A | 12/1967 | Sinclair |
| 3,447,164 A | 6/1969 | Greenhouse |
| D215,751 S | 10/1969 | Castelliano |
| 3,491,374 A | 1/1970 | Frangos |
| 3,535,282 A | 10/1970 | Mallory |
| 3,537,909 A | 11/1970 | Horton |
| 3,602,759 A | 8/1971 | Evans |
| 3,634,676 A | 1/1972 | Castellano |
| 3,647,059 A | 3/1972 | Humphreys |
| 3,666,901 A | 5/1972 | Weinhart |
| 3,683,168 A | 8/1972 | Tatje |
| 3,749,902 A | 7/1973 | Drew |
| 3,769,663 A | 11/1973 | Perl |
| D229,975 S | 1/1974 | Klugmann |
| 3,793,517 A | 2/1974 | Carlini |
| 3,845,389 A | 10/1974 | Phillips |
| 3,947,676 A | 3/1976 | Battilana |
| 3,963,917 A | 6/1976 | Romano |
| 4,005,776 A | 2/1977 | Seeley |
| 4,011,600 A | 3/1977 | Malk |
| 4,053,688 A | 10/1977 | Perkins |
| 4,092,704 A | 5/1978 | Malm |
| 4,176,932 A | 12/1979 | Young |
| 4,186,429 A | 1/1980 | Johnston |
| 4,210,952 A | 7/1980 | Ressmeyer |
| 4,231,079 A | 10/1980 | Heminover |
| 4,254,451 A | 3/1981 | Cochran |
| 4,268,894 A | 5/1981 | Bartunek |
| 4,270,227 A | 6/1981 | Wolfe |
| 4,283,127 A | 8/1981 | Rosenwinkel |
| 4,298,913 A | 11/1981 | Lozar |
| 4,317,162 A | 2/1982 | Richards et al. |
| 4,332,007 A | 5/1982 | Gibstein |
| 4,364,107 A | 12/1982 | Wieczorek |
| 4,392,183 A | 7/1983 | Ostlund |
| 4,398,237 A | 8/1983 | Doyel |
| 4,406,040 A | 9/1983 | Cannone |
| 4,425,531 A | 1/1984 | Holmes |
| D272,733 S | 2/1984 | Cosmos |
| 4,430,532 A | 2/1984 | Matsumoto |
| 4,442,478 A | 4/1984 | Stansbury |
| 4,462,064 A | 7/1984 | Schweitzer |
| 4,470,263 A | 9/1984 | Lehovec |
| 4,483,021 A | 11/1984 | McCall |
| 4,516,157 A | 5/1985 | Campbell |
| 4,521,831 A | 6/1985 | Thayer |
| 4,541,698 A | 9/1985 | Lerner |
| 4,551,857 A | 11/1985 | Galvin |
| 4,559,516 A | 12/1985 | Schott |
| 4,570,206 A | 2/1986 | Deutsch |
| 4,602,191 A | 7/1986 | Davila |
| 4,604,760 A | 8/1986 | Coin |
| 4,616,297 A | 10/1986 | Liu |
| 4,631,644 A | 12/1986 | Dannhauer |
| 4,638,410 A | 1/1987 | Barker |
| 4,641,647 A | 2/1987 | Behan |
| 4,642,817 A | 2/1987 | Ferstenfeld |
| 4,665,568 A | 5/1987 | Stutes |
| 4,667,274 A | 5/1987 | Daniel |
| 4,669,610 A | 6/1987 | Lindsey |
| 4,680,815 A | 7/1987 | Hirsch |
| 4,774,643 A | 9/1988 | McGinnis |
| 4,794,496 A | 12/1988 | Lanes |
| 4,817,212 A | 4/1989 | Benoit |
| 4,822,160 A | 4/1989 | Tsai |
| 4,822,161 A | 4/1989 | Jimmy |
| 4,827,384 A | 5/1989 | VonSchlemmer |
| 4,829,285 A | 5/1989 | Brand |
| 4,872,218 A | 10/1989 | Holt |
| 4,875,147 A | 10/1989 | Auer |
| 4,884,067 A | 11/1989 | Nordholm |
| 4,901,210 A | 2/1990 | Hanabusa |
| 4,901,211 A | 2/1990 | Shen |
| 4,902,119 A | 2/1990 | Porsche |
| 4,904,078 A | 2/1990 | Gorike |
| 4,920,466 A * | 4/1990 | Liu ............... A61H 23/0263 362/105 |
| 4,945,458 A | 7/1990 | Batts |
| 4,951,068 A | 8/1990 | Ichikawa |
| 4,959,760 A | 9/1990 | Wu |
| 4,963,045 A | 10/1990 | Willcox |
| 4,969,069 A * | 11/1990 | Eichost ............... F21V 33/0052 362/105 |
| 4,991,068 A | 2/1991 | Mickey |
| 4,998,187 A | 3/1991 | Herrick |
| 5,003,640 A | 4/1991 | Pizzacar |
| D316,932 S | 5/1991 | Escher, Jr. |
| 5,039,829 A | 8/1991 | Brucksch |
| 5,060,814 A | 10/1991 | Oglesbee |
| 5,068,771 A | 11/1991 | Savage, Jr. |
| 5,070,436 A | 12/1991 | Alexander |
| 5,088,127 A | 2/1992 | Thornock |
| 5,111,366 A | 5/1992 | Rife |
| 5,113,325 A | 5/1992 | Eisenbraun |
| 5,117,510 A | 6/1992 | Broussard |
| 5,122,943 A | 6/1992 | Pugh |
| 5,138,538 A | 8/1992 | Sperling |
| 5,140,116 A | 8/1992 | Schmitt-Walter |
| 5,140,220 A | 8/1992 | Hasegawa |
| 5,143,443 A | 9/1992 | Madsen |
| 5,158,356 A | 10/1992 | Guthrie |
| 5,163,420 A | 11/1992 | VanDerBel |
| 5,164,749 A | 11/1992 | Shelton |
| 5,165,789 A | 11/1992 | Womack |
| 5,183,326 A | 2/1993 | Case |
| 5,189,512 A | 2/1993 | Cameron |
| 5,193,220 A | 3/1993 | Ichinohe |
| 5,193,347 A | 3/1993 | Apisdorf |
| 5,207,500 A | 5/1993 | Rios |
| 5,218,385 A | 6/1993 | Lii |

(56) References Cited

U.S. PATENT DOCUMENTS

| | | |
|---|---|---|
| 5,224,772 A | 7/1993 | Fustos |
| 5,230,558 A | 7/1993 | Jong |
| 5,238,344 A | 8/1993 | Nagayama |
| 5,245,516 A | 9/1993 | deHaas |
| 5,249,675 A | 10/1993 | Strauss |
| D343,470 S | 1/1994 | Yuen |
| 5,278,734 A | 1/1994 | Ferber |
| D349,123 S | 7/1994 | Cooley |
| 5,329,637 A | 7/1994 | Walker |
| 5,331,333 A | 7/1994 | Tagawa |
| 5,331,357 A | 7/1994 | Cooley |
| 5,353,205 A * | 10/1994 | Hudak ............... A42B 3/0446 2/200.2 |
| 5,357,409 A | 10/1994 | Glatt |
| 5,363,291 A | 11/1994 | Steiner |
| 5,367,345 A | 11/1994 | da Silva |
| 5,404,593 A | 4/1995 | Kronenberger |
| 5,408,393 A | 4/1995 | Becker |
| 5,410,746 A | 4/1995 | Gelber |
| 5,412,545 A | 5/1995 | Rising |
| 5,418,565 A | 5/1995 | Smith |
| 5,423,419 A | 6/1995 | Wentz |
| 5,438,698 A | 8/1995 | Burton |
| 5,452,190 A | 9/1995 | Priesemuth |
| 5,460,346 A | 10/1995 | Hirsch |
| 5,463,538 A | 10/1995 | Womack |
| 5,467,992 A | 11/1995 | Harkness |
| 5,485,358 A | 1/1996 | Chien |
| 5,488,361 A | 1/1996 | Perry |
| 5,503,637 A | 4/1996 | Kyricos |
| 5,508,900 A | 4/1996 | Norman |
| 5,510,961 A | 4/1996 | Peng |
| 5,541,767 A | 7/1996 | Murphy |
| 5,541,816 A | 7/1996 | Miserendino |
| 5,542,627 A | 8/1996 | Crenshaw |
| 5,546,099 A | 8/1996 | Quint |
| 5,564,128 A | 10/1996 | Richardson |
| 5,567,038 A | 10/1996 | Lary |
| D375,372 S | 11/1996 | Allen |
| 5,575,554 A | 11/1996 | Guritz |
| 5,601,358 A | 2/1997 | Chien |
| 5,606,743 A | 2/1997 | Vogt |
| 5,608,808 A | 3/1997 | da Silva |
| 5,610,678 A | 3/1997 | Tsuboi |
| 5,644,189 A | 7/1997 | Busby |
| 5,655,374 A | 8/1997 | Santilli |
| D383,754 S | 9/1997 | Yuen |
| D383,863 S | 9/1997 | Yuen |
| 5,667,291 A | 9/1997 | Caplan |
| 5,667,292 A | 9/1997 | Sabalvaro, Jr. |
| 5,676,449 A | 10/1997 | Newsome |
| 5,677,079 A | 10/1997 | DeZorzi |
| 5,680,718 A | 10/1997 | Ratcliffe |
| 5,688,039 A | 11/1997 | Johnson |
| D388,113 S | 12/1997 | Feinbloom |
| 5,692,244 A | 12/1997 | Johnson |
| 5,708,449 A | 1/1998 | Heacock |
| 5,709,464 A | 1/1998 | Tseng |
| 5,718,335 A | 2/1998 | Boudreaux |
| 5,722,762 A | 3/1998 | Soll |
| 5,730,290 A | 3/1998 | Futo |
| 5,741,060 A | 4/1998 | Johnson |
| 5,743,621 A | 4/1998 | Mantha |
| 5,758,947 A | 6/1998 | Glatt |
| 5,774,338 A | 6/1998 | Wessling, III |
| 5,786,665 A | 7/1998 | Ohtsuki |
| 5,800,278 A | 9/1998 | Varriano |
| 5,806,961 A | 9/1998 | Dalton |
| 5,822,636 A | 10/1998 | Cho |
| 5,829,063 A | 11/1998 | Cheng |
| 5,829,860 A | 11/1998 | Lawther |
| 5,836,673 A | 11/1998 | Lo |
| 5,845,778 A | 12/1998 | Hickey, Jr. |
| 5,845,987 A | 12/1998 | Painter |
| 5,857,220 A | 1/1999 | Erny |
| 5,865,333 A | 2/1999 | Wolfe |
| 5,871,271 A | 2/1999 | Chien |
| D407,187 S | 3/1999 | Makki |
| 5,876,241 A | 3/1999 | Frantz |
| 5,893,631 A | 4/1999 | Padden |
| 5,894,604 A | 4/1999 | Crabb |
| 5,918,966 A | 7/1999 | Arnold |
| 5,920,910 A | 7/1999 | Calvo |
| 5,921,674 A | 7/1999 | Koczi |
| 5,922,489 A | 7/1999 | Adachi |
| 5,931,693 A | 8/1999 | Yamazaki |
| 5,946,071 A | 8/1999 | Feldman |
| 5,982,969 A | 11/1999 | Sugiyama |
| 5,997,165 A | 12/1999 | Lehrer |
| 6,005,536 A | 12/1999 | Beadles |
| 6,007,212 A | 12/1999 | Chan |
| 6,007,213 A | 12/1999 | Baumgartner |
| 6,009,563 A | 1/2000 | Swanson |
| 6,012,822 A | 1/2000 | Robinson |
| 6,012,827 A | 1/2000 | Caplan |
| D420,035 S | 2/2000 | Hartman |
| D420,207 S | 2/2000 | Barton |
| 6,021,525 A | 2/2000 | Mertins |
| 6,023,788 A | 2/2000 | McCallum |
| 6,028,627 A | 2/2000 | Helmsderfer |
| 6,032,291 A | 3/2000 | Asenguah |
| 6,032,293 A | 3/2000 | Makki |
| 6,056,413 A | 5/2000 | Urso |
| D428,431 S | 7/2000 | Jordan |
| 6,086,214 A | 7/2000 | Ridge |
| 6,087,037 A | 7/2000 | Rieder |
| 6,088,053 A | 7/2000 | Hammack |
| 6,094,749 A | 8/2000 | Proctor |
| 6,113,243 A | 9/2000 | Saul |
| 6,113,244 A | 9/2000 | Baumgartner |
| 6,116,745 A | 9/2000 | Yei |
| 6,124,056 A | 9/2000 | Kimura |
| 6,126,294 A | 10/2000 | Koyama |
| 6,167,570 B1 | 1/2001 | Su |
| 6,168,286 B1 | 1/2001 | Duffy |
| 6,172,657 B1 | 1/2001 | Kamakura |
| 6,174,075 B1 | 1/2001 | Fuwausa |
| 6,176,601 B1 | 1/2001 | Nester |
| 6,206,543 B1 | 3/2001 | Henry |
| 6,236,007 B1 | 5/2001 | Ho |
| 6,237,147 B1 | 5/2001 | Brockman |
| 6,240,566 B1 | 6/2001 | Scantlin |
| 6,244,721 B1 | 6/2001 | Rodriguez |
| 6,250,769 B1 | 6/2001 | Kirk |
| D445,928 S | 7/2001 | Sharrah |
| 6,256,795 B1 | 7/2001 | Habel |
| D446,324 S | 8/2001 | Lynch |
| 6,290,368 B1 | 9/2001 | Lehrer |
| 6,299,323 B1 | 10/2001 | Yu |
| 6,302,570 B1 | 10/2001 | Petell |
| 6,306,538 B1 | 10/2001 | Saitoh |
| 6,307,526 B1 | 10/2001 | Mann |
| 6,311,350 B1 | 11/2001 | Kaiserman |
| 6,311,837 B1 | 11/2001 | Blaustein |
| 6,320,822 B1 | 11/2001 | Okeya |
| 6,325,521 B1 | 12/2001 | Gregg |
| 6,328,454 B1 | 12/2001 | Davis |
| 6,340,234 B1 | 1/2002 | Brown, Jr. |
| 6,345,716 B1 | 2/2002 | Chapman |
| 6,347,410 B1 | 2/2002 | Lee |
| 6,363,537 B1 | 4/2002 | Park |
| 6,366,344 B1 | 4/2002 | Lach |
| 6,367,949 B1 | 4/2002 | Pederson |
| D457,670 S | 5/2002 | Allen |
| 6,382,407 B1 | 5/2002 | Chao |
| 6,386,701 B1 | 5/2002 | Khulusi |
| 6,390,640 B1 | 5/2002 | Wong |
| 6,398,386 B1 | 6/2002 | Huang |
| 6,416,199 B1 | 7/2002 | Heine |
| 6,431,904 B1 | 8/2002 | Berelsman |
| 6,439,738 B1 | 8/2002 | Matthews |
| 6,442,764 B1 | 9/2002 | Badillo |
| 6,457,838 B1 | 10/2002 | Dugmore |
| 6,461,015 B1 | 10/2002 | Welch |

(56) References Cited

U.S. PATENT DOCUMENTS

| | | |
|---|---|---|
| 6,461,025 B1 | 10/2002 | Payne |
| 6,474,830 B1 | 11/2002 | Hansen |
| 6,476,391 B1 | 11/2002 | Zhang |
| 6,497,493 B1 | 12/2002 | Theisen |
| D469,198 S | 1/2003 | Olson |
| 6,504,099 B2 | 1/2003 | Huang |
| 6,523,973 B2 | 2/2003 | Galli |
| 6,530,672 B2 | 3/2003 | Galli |
| 6,538,567 B2 | 3/2003 | Stewart |
| D473,890 S | 4/2003 | Waters |
| 6,549,231 B1 | 4/2003 | Matsui |
| 6,553,570 B1 | 4/2003 | Flynn |
| 6,554,444 B2 | 4/2003 | Shimada |
| 6,578,982 B1 | 6/2003 | Lynch |
| D477,432 S | 7/2003 | Parsons |
| 6,598,991 B2 | 7/2003 | Altman |
| 6,604,837 B2 | 8/2003 | Sandberg |
| 6,612,695 B2 | 9/2003 | Waters |
| 6,612,696 B2 | 9/2003 | Waters |
| 6,616,293 B2 | 9/2003 | Mickey |
| 6,634,031 B1 | 10/2003 | Schlapkohl |
| 6,642,667 B2 | 11/2003 | Avis |
| D483,928 S | 12/2003 | Mansell |
| 6,659,618 B2 | 12/2003 | Waters |
| D484,905 S | 1/2004 | Waters |
| 6,679,615 B2 | 1/2004 | Spearing |
| 6,704,044 B1 | 3/2004 | Foster |
| 6,709,142 B2 | 3/2004 | Gyori |
| 6,713,956 B2 | 3/2004 | HsingChen |
| 6,715,309 B1 | 4/2004 | Junkins |
| 6,719,437 B2 | 4/2004 | Lary |
| 6,721,962 B1 | 4/2004 | Polaire |
| D489,165 S | 5/2004 | Waters |
| 6,733,150 B1 | 5/2004 | Hanley |
| 6,749,166 B2 | 6/2004 | Valentine |
| 6,760,925 B1 | 7/2004 | Maxwell |
| 6,764,194 B1 | 7/2004 | Cooper |
| 6,802,636 B1 | 10/2004 | Bailey, Jr. |
| 6,808,284 B1 | 10/2004 | Chao |
| 6,811,441 B2 | 11/2004 | Simpson |
| 6,817,711 B2 | 11/2004 | Schubert |
| 6,830,357 B2 | 12/2004 | Lopez |
| D501,266 S | 1/2005 | Harris |
| 6,837,590 B2 | 1/2005 | Marston |
| 6,857,739 B1 | 2/2005 | Watson |
| 6,860,628 B2 | 3/2005 | Robertson |
| 6,863,416 B2 | 3/2005 | Waters |
| 6,865,285 B1 | 3/2005 | Villa-Aleman |
| 6,880,989 B2 | 4/2005 | Sotome |
| 6,908,208 B1 | 6/2005 | Hyde |
| D507,368 S | 7/2005 | Waters |
| D507,369 S | 7/2005 | Waters |
| 6,918,678 B2 * | 7/2005 | McClanahan ....... F21V 33/0052 362/105 |
| 6,923,322 B2 | 8/2005 | Lenker |
| 6,929,375 B2 | 8/2005 | Satomi |
| 6,929,878 B2 | 8/2005 | Chen |
| 6,932,216 B2 | 8/2005 | Blaustein |
| 6,935,761 B2 | 8/2005 | Vanderschuit |
| 6,941,583 B2 | 9/2005 | Yan |
| 6,966,668 B2 | 11/2005 | Cugini |
| 6,969,178 B2 | 11/2005 | Zuloff |
| 6,977,776 B2 | 12/2005 | Volkenandt |
| 6,993,803 B2 | 2/2006 | Chan |
| 6,994,445 B1 | 2/2006 | Pomes |
| 6,997,552 B1 | 2/2006 | Hung |
| 7,000,841 B2 | 2/2006 | Becker |
| 7,003,353 B1 | 2/2006 | Parkhouse |
| 7,004,439 B1 | 2/2006 | Taylor |
| 7,004,582 B2 | 2/2006 | Jannard |
| 7,008,074 B1 | 3/2006 | Halm |
| 7,021,790 B2 | 4/2006 | Parsons |
| D520,460 S | 5/2006 | Wadsworth |
| 7,052,154 B2 | 5/2006 | Vanderschuit |
| 7,055,179 B2 | 6/2006 | Warner |
| 7,086,749 B1 | 8/2006 | Hanley |
| 7,094,981 B2 | 8/2006 | Sorrentino |
| 7,104,670 B2 | 9/2006 | Waters |
| 7,105,939 B2 | 9/2006 | Bednyak |
| 7,111,956 B2 | 9/2006 | Brown |
| 7,114,823 B2 * | 10/2006 | McCullough ....... F21V 33/0056 362/105 |
| 7,118,241 B2 | 10/2006 | Sohn |
| 7,118,262 B2 | 10/2006 | Negley |
| 7,128,434 B1 | 10/2006 | Nally |
| 7,147,324 B2 | 12/2006 | Jannard |
| 7,147,338 B2 | 12/2006 | Gregg |
| 7,150,526 B2 | 12/2006 | Jannard |
| 7,163,309 B2 | 1/2007 | Sohn |
| 7,182,478 B2 | 2/2007 | Marston |
| 7,186,159 B1 | 3/2007 | Baxter |
| 7,192,151 B2 | 3/2007 | Clupper |
| 7,209,652 B2 | 4/2007 | Uenaka |
| 7,213,917 B2 | 5/2007 | Jannard |
| 7,216,973 B2 | 5/2007 | Jannard |
| 7,226,180 B2 | 6/2007 | Sung |
| 7,234,831 B1 | 6/2007 | Hanley |
| 7,255,437 B2 | 8/2007 | Howell |
| 7,264,350 B2 | 9/2007 | Jannard |
| D553,177 S | 10/2007 | Chen |
| 7,278,734 B2 | 10/2007 | Jannard |
| 7,281,826 B2 | 10/2007 | Huang |
| 7,318,654 B2 * | 1/2008 | McClanahan ....... F21V 33/0052 362/105 |
| 7,331,064 B1 | 2/2008 | Quintal |
| D566,044 S | 4/2008 | DArco |
| D568,922 S | 5/2008 | Anderl |
| 7,369,174 B2 | 5/2008 | Olita |
| 7,377,664 B2 | 5/2008 | Waters |
| 7,377,666 B1 * | 5/2008 | Tyler ...................... A61F 11/14 362/105 |
| 7,427,149 B2 | 9/2008 | Sohn |
| 7,431,472 B2 | 10/2008 | Becker |
| 7,438,409 B2 | 10/2008 | Jordan |
| 7,457,536 B2 | 11/2008 | Hamada |
| 7,461,764 B2 | 12/2008 | Thompson |
| 7,466,040 B2 | 12/2008 | Bruwer |
| 7,470,022 B2 | 12/2008 | Lerner |
| 7,506,992 B2 | 3/2009 | Carter |
| D591,675 S | 5/2009 | Waters |
| 7,562,979 B2 | 7/2009 | Waters |
| 7,576,800 B2 | 8/2009 | Swain |
| D600,208 S | 9/2009 | Waters |
| D600,738 S | 9/2009 | Su |
| 7,598,928 B1 | 10/2009 | Buskop |
| 7,607,775 B2 | 10/2009 | Hermanson |
| 7,609,295 B2 | 10/2009 | Aridome |
| 7,611,255 B1 | 11/2009 | Lagassey |
| 7,621,000 B1 | 11/2009 | Fulton |
| D605,381 S | 12/2009 | Mastrantonio et al. |
| 7,661,818 B2 | 2/2010 | Waters |
| D611,086 S | 3/2010 | Meng-Suen |
| 7,677,751 B2 | 3/2010 | Kinsman |
| 7,699,486 B1 | 4/2010 | Beiner |
| D617,826 S | 6/2010 | Waters |
| 7,753,547 B2 | 7/2010 | Waters |
| 7,755,219 B2 | 7/2010 | Bruwer |
| 7,784,960 B2 | 8/2010 | Lahtinen |
| 7,862,979 B2 | 1/2011 | Morris |
| 7,934,846 B1 | 5/2011 | Schwanz |
| 7,938,553 B1 | 5/2011 | Beiner |
| 7,942,543 B2 | 5/2011 | Ritter |
| 8,002,437 B2 | 8/2011 | Sohn |
| 8,075,153 B2 * | 12/2011 | Werner .................. A61F 11/14 128/866 |
| 8,141,395 B2 | 3/2012 | Dillavou |
| 8,157,403 B2 | 4/2012 | Lau |
| D659,351 S | 5/2012 | Benkendorfer |
| 8,333,485 B2 | 12/2012 | Waters |
| 8,364,220 B2 | 1/2013 | Sandmore |
| 8,388,164 B2 | 3/2013 | Waters |
| 8,491,145 B2 | 7/2013 | Waters |
| 8,550,651 B2 | 10/2013 | Waters |
| 8,698,027 B2 | 4/2014 | Anderst |

(56) References Cited

U.S. PATENT DOCUMENTS

| | | |
|---|---|---|
| 8,757,931 B2 | 6/2014 | Püttmann |
| 8,769,723 B1 | 7/2014 | Ilges |
| 8,774,420 B2 * | 7/2014 | Belafonte ............ H04R 1/2811 381/182 |
| 8,813,268 B1 | 8/2014 | Fitzgerald et al. |
| 8,919,984 B1 | 12/2014 | Fitzgerald |
| 8,950,012 B2 | 2/2015 | Ilges et al. |
| 9,057,500 B2 | 6/2015 | Opolka |
| D734,925 S | 7/2015 | Waters |
| 2001/0024365 A1 | 9/2001 | Aknine |
| 2002/0027777 A1 * | 3/2002 | Takasu ................... F21L 14/00 362/105 |
| 2002/0129989 A1 * | 9/2002 | Parsons ................... A61B 7/02 181/131 |
| 2002/0131275 A1 | 9/2002 | Yamamoto |
| 2002/0159250 A1 | 10/2002 | Kuo |
| 2002/0163800 A1 | 11/2002 | Hansen |
| 2002/0186557 A1 | 12/2002 | Lary |
| 2002/0187806 A1 | 12/2002 | Jang |
| 2003/0079387 A1 | 5/2003 | Derose |
| 2003/0086053 A1 | 5/2003 | Waters |
| 2003/0086054 A1 | 5/2003 | Waters |
| 2003/0106918 A1 | 6/2003 | Hung |
| 2003/0122958 A1 | 7/2003 | Olita |
| 2003/0151910 A1 | 8/2003 | Marston |
| 2003/0169207 A1 | 9/2003 | Beigel |
| 2003/0189824 A1 | 10/2003 | Meeder |
| 2003/0206269 A1 | 11/2003 | Waters |
| 2003/0231489 A1 | 12/2003 | Hsiao |
| 2004/0001150 A1 | 1/2004 | Schindler |
| 2004/0008157 A1 | 1/2004 | Brubaker |
| 2004/0085745 A1 | 5/2004 | Yoshihara |
| 2004/0128737 A1 | 7/2004 | Gesten |
| 2004/0141312 A1 | 7/2004 | Henning |
| 2004/0141316 A1 | 7/2004 | Twardawski |
| 2004/0165109 A1 | 8/2004 | Lee |
| 2004/0222638 A1 | 11/2004 | Bednyak |
| 2004/0240067 A1 | 12/2004 | Marusi |
| 2004/0240204 A1 | 12/2004 | Russ |
| 2004/0264176 A1 | 12/2004 | Vanderschuit |
| 2005/0001433 A1 | 1/2005 | Seelin |
| 2005/0035925 A1 | 2/2005 | Ostromek |
| 2005/0047116 A1 | 3/2005 | Gagne |
| 2005/0066422 A1 | 3/2005 | Yan |
| 2005/0072458 A1 | 4/2005 | Goldstein |
| 2005/0078473 A1 | 4/2005 | Zuloff |
| 2005/0083676 A1 | 4/2005 | VanderSchuit |
| 2005/0099799 A1 | 5/2005 | Cugini |
| 2005/0105285 A1 | 5/2005 | Maden |
| 2005/0161313 A1 | 7/2005 | Sorrentino |
| 2005/0174753 A1 | 8/2005 | Cao |
| 2005/0204490 A1 | 9/2005 | Kemp |
| 2005/0211187 A1 | 9/2005 | Harman |
| 2005/0211574 A1 | 9/2005 | Reeve |
| 2005/0213340 A1 | 9/2005 | Suzuki |
| 2005/0219837 A1 | 10/2005 | Brown |
| 2005/0226433 A1 * | 10/2005 | McClanahan ....... F21V 33/0052 381/71.6 |
| 2005/0237479 A1 | 10/2005 | Rose |
| 2005/0248932 A1 | 11/2005 | Waters |
| 2005/0254238 A1 | 11/2005 | Parker |
| 2005/0265015 A1 | 12/2005 | Salazar |
| 2006/0012974 A1 | 1/2006 | Su |
| 2006/0012975 A1 | 1/2006 | Huttner |
| 2006/0037125 A1 | 2/2006 | McDowell |
| 2006/0091784 A1 | 5/2006 | Conner |
| 2006/0092621 A1 | 5/2006 | Lai |
| 2006/0093264 A1 | 5/2006 | Tabuchi |
| 2006/0107952 A1 | 5/2006 | Schlosser |
| 2006/0125624 A1 | 6/2006 | Ostrovsky |
| 2006/0126323 A1 | 6/2006 | Pomes |
| 2006/0138440 A1 | 6/2006 | Jyo |
| 2006/0141828 A1 | 6/2006 | Dean |
| 2006/0157569 A1 | 7/2006 | Becker |
| 2006/0158895 A1 | 7/2006 | Brands |
| 2006/0165160 A1 | 7/2006 | Winningstad |
| 2006/0198122 A1 | 9/2006 | Senter |
| 2006/0212994 A1 | 9/2006 | Proctor |
| 2006/0215393 A1 | 9/2006 | VanderSchuit |
| 2006/0232955 A1 | 10/2006 | Labine |
| 2006/0238995 A1 | 10/2006 | Wang |
| 2006/0239018 A1 | 10/2006 | Jardin |
| 2006/0263677 A1 | 11/2006 | Tsai |
| 2006/0285315 A1 | 12/2006 | Tufenkjian |
| 2006/0286443 A1 | 12/2006 | Huang |
| 2006/0291193 A1 | 12/2006 | Hill |
| 2007/0003826 A1 | 1/2007 | Hsu |
| 2007/0013865 A1 | 1/2007 | Jordan |
| 2007/0030442 A1 | 2/2007 | Howell |
| 2007/0048598 A1 | 3/2007 | Huang |
| 2007/0053179 A1 | 3/2007 | Pang |
| 2007/0058361 A1 | 3/2007 | Sevilla |
| 2007/0064413 A1 | 3/2007 | Slater |
| 2007/0072655 A1 | 3/2007 | Cascone |
| 2007/0074752 A1 | 4/2007 | Shau |
| 2007/0086182 A1 | 4/2007 | Kelly |
| 2007/0097668 A1 | 5/2007 | Choi |
| 2007/0127250 A1 | 6/2007 | Waters |
| 2007/0140675 A1 | 6/2007 | Yanagi |
| 2007/0145746 A1 | 6/2007 | Biamonte |
| 2007/0153500 A1 | 7/2007 | Waters |
| 2007/0153537 A1 | 7/2007 | Scott |
| 2007/0159810 A1 | 7/2007 | Kim |
| 2007/0159823 A1 | 7/2007 | Ho |
| 2007/0171628 A1 | 7/2007 | Seade |
| 2007/0189003 A1 | 8/2007 | Daley |
| 2007/0206373 A1 | 9/2007 | Whiteside |
| 2007/0236649 A1 | 10/2007 | Lin |
| 2007/0236915 A1 | 10/2007 | Chen |
| 2007/0236916 A1 | 10/2007 | Hsu |
| 2008/0049963 A1 * | 2/2008 | Mann ..................... H02J 7/0044 381/384 |
| 2008/0069391 A1 | 3/2008 | Steyn |
| 2008/0130272 A1 | 6/2008 | Waters |
| 2008/0152482 A1 | 6/2008 | Patel |
| 2008/0186705 A1 | 8/2008 | Liu |
| 2008/0263750 A1 | 10/2008 | Chen |
| 2008/0266839 A1 | 10/2008 | Claypool |
| 2009/0010474 A1 * | 1/2009 | Ouryouji ............... H04R 1/1058 381/370 |
| 2009/0126076 A1 | 5/2009 | Ochoa |
| 2009/0147503 A1 | 6/2009 | Bennett |
| 2009/0148149 A1 | 6/2009 | Chishima |
| 2009/0193566 A1 | 8/2009 | Waters |
| 2009/0213323 A1 | 8/2009 | Mermanson |
| 2009/0268936 A1 * | 10/2009 | Goldberg ............. H04R 1/1041 381/384 |
| 2009/0323317 A1 | 12/2009 | Spartano |
| 2010/0024091 A1 | 2/2010 | Mehtab |
| 2010/0095431 A1 | 4/2010 | Liao |
| 2010/0134761 A1 | 6/2010 | Johns |
| 2010/0182563 A1 | 7/2010 | Waters |
| 2010/0214767 A1 | 8/2010 | Waters |
| 2010/0242155 A1 | 9/2010 | Carullo |
| 2010/0307931 A1 | 12/2010 | Waters |
| 2010/0313335 A1 | 12/2010 | Waters |
| 2011/0013135 A1 | 1/2011 | Waters |
| 2011/0075095 A1 | 3/2011 | Waters |
| 2011/0122601 A1 | 5/2011 | Waters |
| 2011/0187989 A1 | 8/2011 | Waters |
| 2011/0210685 A1 | 9/2011 | Liao |
| 2011/0211156 A1 | 9/2011 | Beiner |
| 2011/0228211 A1 | 9/2011 | Waters |
| 2012/0014095 A2 | 1/2012 | Waters |
| 2012/0098465 A1 | 4/2012 | Rothschild |
| 2013/0025612 A1 | 1/2013 | Hunter |
| 2013/0111651 A1 | 5/2013 | Waters |
| 2013/0192961 A1 | 8/2013 | Waters |
| 2013/0198935 A1 | 8/2013 | Waters |
| 2014/0049947 A1 | 2/2014 | Lombard |
| 2014/0101827 A1 | 4/2014 | Dennis |
| 2014/0173807 A1 | 6/2014 | Waters |
| 2014/0237706 A1 | 8/2014 | OConner |
| 2014/0268683 A1 | 9/2014 | Waters |

(56) References Cited

U.S. PATENT DOCUMENTS

| | | | |
|---|---|---|---|
| 2014/0270685 A1 | 9/2014 | Letke | |
| 2015/0358515 A1 | 12/2015 | Resnick | |
| 2016/0337745 A1* | 11/2016 | Adams | H04R 1/1041 |

FOREIGN PATENT DOCUMENTS

| | | |
|---|---|---|
| AU | 199940150 | 2/2000 |
| AU | 199959545 | 3/2000 |
| AU | 2002100976 | 6/2003 |
| AU | 2003100277 | 7/2003 |
| AU | 2003248016 | 11/2004 |
| CA | 2029772 | 5/1991 |
| CA | 2198625 | 2/1997 |
| CA | 2184336 | 5/1997 |
| CA | 2406450 | 11/2001 |
| CA | 2466175 A1 | 5/2003 |
| CA | 2608746 A1 | 11/2006 |
| CA | 2610073 A1 | 5/2008 |
| CN | 86208973 | 10/1987 |
| CN | 2173427 | 8/1994 |
| CN | 2239167 | 11/1996 |
| CN | 2423761 | 3/2001 |
| CN | 2433836 | 6/2001 |
| CN | 2458892 | 11/2001 |
| CN | 2508592 | 9/2002 |
| CN | 2544551 | 4/2003 |
| CN | 1462597 | 12/2003 |
| CN | 1603677 A | 4/2005 |
| CN | 101950091 A | 1/2011 |
| CN | 301445845 S | 1/2011 |
| DE | 3043007 | 6/1982 |
| DE | 8230583 | 9/1983 |
| DE | 9410886 | 9/1994 |
| DE | 29808222 | 11/1998 |
| DE | 19837151 | 4/2000 |
| DE | 20007738 | 9/2000 |
| DE | 29915607 | 9/2000 |
| DE | 20017922 | 2/2001 |
| DE | 20101380 | 8/2001 |
| DE | 20106261 | 9/2001 |
| DE | 20111815 | 11/2001 |
| DE | 10046295 | 3/2002 |
| DE | 20117740 | 4/2002 |
| DE | 20201557 | 5/2002 |
| DE | 20200058 | 6/2002 |
| DE | 10103591 | 8/2002 |
| DE | 20110124 | 8/2002 |
| DE | 10057388 | 9/2002 |
| DE | 20209115 | 10/2002 |
| DE | 20210806 | 10/2002 |
| DE | 10216152 | 12/2002 |
| DE | 20209611 | 1/2003 |
| DE | 20313629 | 12/2003 |
| DE | 10330589 | 1/2004 |
| DE | 20319297 | 2/2004 |
| DE | 20318860 | 4/2004 |
| DE | 20318949 | 4/2004 |
| DE | 202004004960 | 9/2005 |
| DE | 102007006860 A1 | 8/2007 |
| EP | 1072204 | 1/2001 |
| EP | 1374707 | 1/2004 |
| EP | 2290433 A1 | 3/2011 |
| EP | 2299311 A1 | 3/2011 |
| FR | 1221782 | 6/1960 |
| FR | 2798721 | 3/2001 |
| FR | 2824709 | 11/2002 |
| FR | 2829365 | 3/2003 |
| FR | 2833068 | 6/2003 |
| FR | 2833069 | 6/2003 |
| GB | 2268043 | 1/1994 |
| GB | 2272073 A | 5/1994 |
| GB | 2316293 | 2/1998 |
| GB | 2358575 | 8/2001 |
| GB | 2363314 | 12/2001 |
| GB | 2374401 | 10/2002 |
| GB | 2378117 | 2/2003 |
| GB | 2378118 | 2/2003 |
| GB | 2388298 | 11/2003 |
| JP | S61006304 | 1/1986 |
| JP | 4289602 | 10/1992 |
| JP | H08027610 A | 1/1996 |
| JP | H08298004 A | 11/1996 |
| JP | H09209210 A | 8/1997 |
| JP | H09296319 A | 11/1997 |
| JP | H10081275 A | 3/1998 |
| JP | H10331019 A | 12/1998 |
| JP | 2001131818 A | 5/2001 |
| JP | 3084061 | 11/2001 |
| JP | 3090973 | 10/2002 |
| JP | 2004207580 | 7/2004 |
| JP | 2004346470 | 12/2004 |
| JP | 2005216832 A | 8/2005 |
| JP | 2006097156 A | 4/2006 |
| JP | 2007119980 | 5/2007 |
| JP | 2008542558 | 11/2008 |
| KR | 200164075 | 2/2000 |
| KR | 200168826 | 2/2000 |
| KR | 200260980 | 1/2002 |
| KR | 20020065405 | 8/2002 |
| KR | 200331201 | 10/2003 |
| TW | 241462 | 2/1995 |
| TW | 275188 | 5/1996 |
| TW | 286489 | 9/1996 |
| TW | 324234 | 1/1998 |
| TW | 329607 | 4/1998 |
| TW | 386364 | 4/2000 |
| WO | 9402043 | 2/1994 |
| WO | 9704434 | 2/1997 |
| WO | 0177575 A1 | 10/2001 |
| WO | 0244611 | 6/2002 |
| WO | 02062165 | 8/2002 |
| WO | 02074398 | 9/2002 |
| WO | 02077520 | 10/2002 |
| WO | 03040808 A2 | 5/2003 |
| WO | 03047377 | 6/2003 |
| WO | 03083811 | 10/2003 |
| WO | 04000054 | 12/2003 |
| WO | 2004064555 | 5/2004 |
| WO | 2004103104 | 12/2004 |
| WO | 2005002378 | 1/2005 |
| WO | 2005005882 | 1/2005 |
| WO | 2005038337 | 4/2005 |
| WO | 2005096856 | 10/2005 |
| WO | 2005098314 | 10/2005 |
| WO | 2006037845 | 4/2006 |
| WO | 2006124928 | 11/2006 |
| WO | 2007073047 | 6/2007 |
| WO | 2007073219 | 6/2007 |
| WO | 2007089236 | 8/2007 |
| WO | 2007093348 | 8/2007 |
| WO | 2007112338 | 10/2007 |
| WO | 2008011750 | 1/2008 |
| WO | 2009079656 A2 | 6/2009 |
| WO | 2010099504 | 9/2010 |
| WO | 2011041591 A1 | 4/2011 |
| WO | 2011100471 A1 | 8/2011 |
| WO | 2011137400 | 11/2011 |
| WO | 2011137406 | 11/2011 |
| WO | 2013096895 | 6/2013 |
| WO | 2013096904 | 6/2013 |

OTHER PUBLICATIONS

"4 LED Lighted Fleece Beanie; POWERCAP," article posted on-line to WISE-SHOP.ca. Added to the businesses catalog on Nov. 6, 2013. Retrieved from the Internet on Jun. 17, 2014. URL: http://www.wise-shop.ca/product_info.php?products_id=489.

"Panther Vision Powercap LED Lighted Beanie," article posted on-line and available for sale at Dick's Sporting Goods with reviews posted as early as Nov. 14, 2014. Retrieved from the Internet on Mar. 9, 2015. URL: http://www.dickssportinggoods.com/product/index.jsp?productId=52376526. (4 pages).

(56) References Cited

OTHER PUBLICATIONS

"Powercap Beanie," article posted on-line to Panther Vision. Publication date unknown. Retrieved from the Internet on Mar. 9, 2015. URL: http://www.panther-vision-promotional-products.com/Prod-18-1-96-10/powercap-trade-beanie.htm. (2 pages).
Extended European search report issued in the related European Application No. 08 86 2753.4 dated Dec. 7, 2012 (7 pages).
Extended European search report issued in the related European Application No. 10 18 1592.6 dated Jan. 31, 2011 (7 pages).
Extended European search report issued in the related European Application No. 10 18 1593.4 dated Feb. 1, 2011 (8 pages).
International Search Report from the International Bureau of WIPO issued in the related International Application No. PCT/US02/35665, dated Jun. 27, 2003, 1 page.
Notification Concerning Transmittal of International Preliminary Report on Patentability and the Written Opinion of the International Searching Authority from the International Bureau of WIPO for International Application No. PCT/US2013/076689, dated Jul. 2, 2015, 7 pages.
Notification of Transmittal of the International Search Report and the Written Opinion of the International Searching Authority, or the Declaration from the International Bureau of WIPO for International Application No. PCT/US10/50978, dated Dec. 3, 2010, 16 pages.
Notification of Transmittal of the International Search Report and the Written Opinion of the International Searching Authority, or the Declaration from the International Bureau of WIPO for International Application No. PCT/US14/28613, 13 pages.
Notification of Transmittal of the International Search Report and the Written Opinion of the International Searching Authority, or the Declaration from the International Bureau of WIPO for International Application No. PCT/US2008/087542 dated May 4, 2009, 12 pages.
Notification of Transmittal of the International Search Report and the Written Opinion of the International Searching Authority, or the Declaration from the International Bureau of WIPO for International Application No. PCT/US2010/025689 dated May 4, 2010, 14 pages.
Notification of Transmittal of the International Search Report and the Written Opinion of the International Searching Authority, or the Declaration from the International Bureau of WIPO for International Application No. PCT/US2011/024400, dated Apr. 29, 2011, 13 pages.
Notification of Transmittal of the International Search Report and the Written Opinion of the International Searching Authority, or the Declaration from the International Bureau of WIPO for International Application No. PCT/US2011/034686 dated Aug. 1, 2011, 16 pages.
Notification of Transmittal of the International Search Report and the Written Opinion of the International Searching Authority, or the Declaration from the International Bureau of WIPO for International Application No. PCT/US2011/051596, dated Jan. 18, 2012, 9 pages.
Notification of Transmittal of the International Search Report and the Written Opinion of the International Searching Authority, or the Declaration from the International Bureau of WIPO for related International Application No. PCT/US2011/034695 dated Oct. 28, 2011, 12 pages.
Office Action issued in related Canadian Application No. 2,466,175 dated Sep. 22, 2010 (3 pages).
Office Action issued in related European Application No. 02 778 755.5 dated Feb. 20, 2007 (7 pages).
Office Action issued in related Japanese Application No. 2010-539834 dated Mar. 19, 2013 and English translation of the same (10 pages).
Patent Examination Report issued in related Australian Application No. 2008338320 dated Nov. 1, 2012 (5 pages).
Supplementary European search report issued in the related European Application No. 02 77 8755 dated Jan. 19, 2005 (2 pages).
Written Opinion of the International Searching Authority and International Search Report from the International Bureau of WIPO for International Application No. PCT/US2006/018968, dated Oct. 16, 2006, 12 pages.
Written Opinion of the International Searching Authority and International Search Report from the International Bureau of WIPO for International Application No. PCT/US2006/018968, dated Oct. 16, 2006, 7 pages.
Written Opinion of the International Searching Authority and International Search Report from the International Bureau of WIPO for International Application No. PCT/US2008/087542, dated May 4, 2009, 12 pages.
Notification of Transmittal of the International Search Report and the Written Opinion of the International Searching Authority, or the Declaration from the International Bureau of WIPO for International Application No. PCT/US2014/028945 dated Jul. 31, 2014, 9 pages.

\* cited by examiner

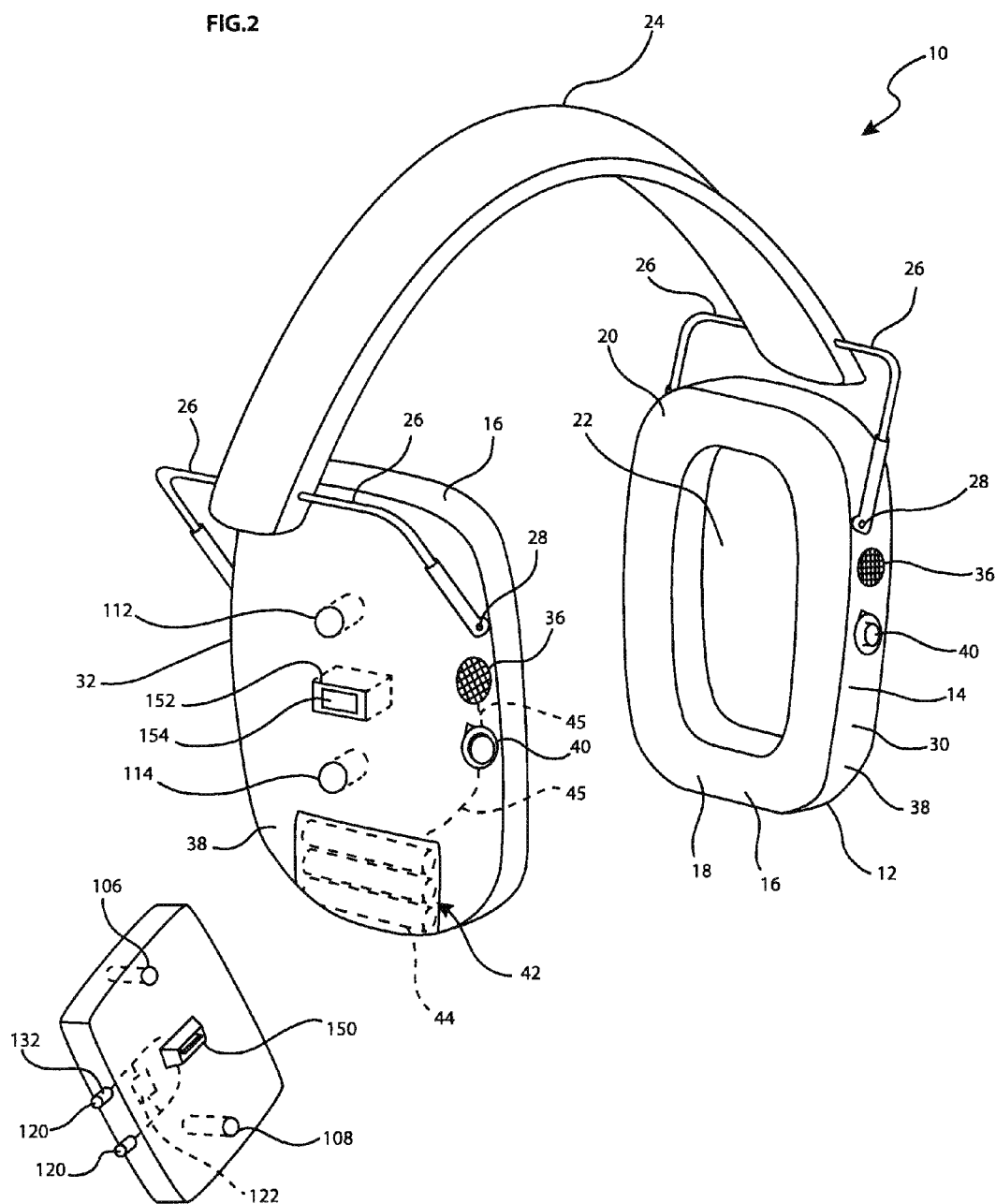

LIGHTED HEADGEAR

CROSS-REFERENCE To RELATED APPLICATIONS

This application claims the benefit of U.S. application No. 61/794,017, filed Mar. 15, 2013, which is hereby incorporated by reference herein in its entirety.

FIELD

This disclosure relates generally to lighted clothing and, more specifically, to lighted headgear.

BACKGROUND

Hearing protection is recommended for loud environments, such as 85 dB or more, to prevent ear damage. Even at lower sound levels, hearing protection can reduce fatigue due to frequent exposure to sound. One type of hearing protection is earmuffs. Earmuffs include cups that extend over a user's ears that are connected by a headband or other headpiece connecting structure. Earmuffs can be active, which include an electronic sound dampening device, and passive, which do not include any electronic dampening assistance.

Headphones for listening to audio are also utilized by consumers during a variety of activities including jogging, working, reading, traveling, and the like.

BRIEF DESCRIPTION OF THE DRAWINGS

FIG. 2 is a perspective view of lighted headgear showing ear covering assemblies connected by a headband and a light module configured to plug into the ear covering assembly to receive power thereby;

DETAILED DESCRIPTION OF THE PREFERRED EMBODIMENTS

Lighted headgear, and more particularly lighted earwear such as earmuffs or headphones, is provided herein that are configured to mount or secure to a user's head while providing light forwardly thereof. The lighted headgear includes ear engaging or covering assemblies, which can be connected by a headband or other crown portion. The ear covering assemblies can include one or more light sources mounted thereto or can have a light module secured thereto to provide a user with hands-free lighting, as will be described below. The disclosure herein can apply to any similarly configured structure, such as hearing protection attached to headgear, including helmets, hats, visors, or the like, earmuffs intended for protection against cold weather, stereo headphones, or the like.

The lighted earwear disclosed herein is particularly advantageous because it provides convenient hands-free lighting for all of the activities a user can engage in while wearing earmuffs, hearing protection, headphones, and the like. For example, a person traveling and listening to music or trying to block out the sound of engines can have forwardly directed lighting for reading, writing, or other activities; a user that works around loud machinery, such as airport workers, construction workers, mechanics, and the like, can have hands-free forwardly directed lighting for working at night or working in poorly lit areas; and a person running or walking outside at night can use the hands free lighting to light a safe path of travel or utilize the lights as a safety device to warn others of their presence.

Figure 1A:
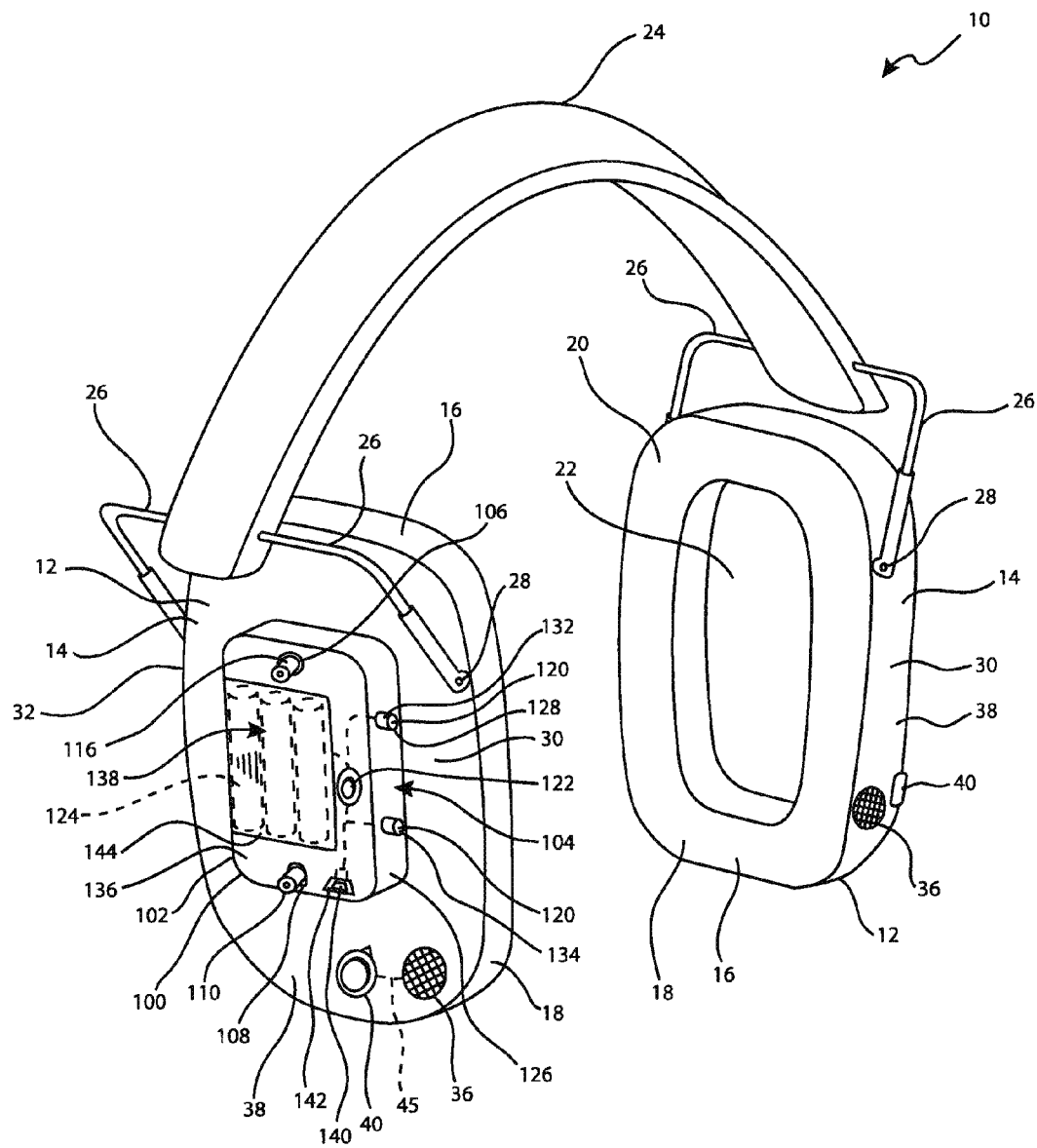
FIG. 1A is a perspective view of lighted headgear showing ear covering assemblies connected by a headband and light modules mounted to the ear covering assemblies to project light forwardly thereof.

As shown in FIG. 1, lighted headgear or earmuffs 10 include two ear covering assemblies or cups 12 having a substantially rigid backing 14 and softer earpads 16 that are configured to abut or encompass and surround the ears of a user. In the illustrated form, the earpads 16 include an ear spanning portion 22 that is configured to engage or be spaced outwardly from a user's ear. With ear encompassing devices, the earpads 16 further include an inwardly projecting portion having a circular or ellipsoid configuration with inwardly facing surfaces 20 that are configured to abut and seal to a user's head around their ears. So configured, the earpad 16 encompasses the ear so that vibrations and sound waves have to travel through the ear protection of the cups 12.

The cups 12 are connected by a headband 24 that is configured to extend over and around the top or side of a head of a user to position the cups 12 adjacent the user's ears. The headband 24 can rest on the user's head or be spaced therefrom. As stated above, the cups 12 can instead be connected to other headgear, such as helmets, hats, visors, or the like. If desired, the headband 24 can pivotably connect to the cups 12, such as with arms 26 extending from the headband 24 to pivot connections 28 at forward and rearward surfaces 30, 32 of the cups 12. The pivot connections 28 allow the cups 12 to more be accurately positioned adjacent to the side of a user's head. The headband 24 can also be adjustable to better position the cups 12 on a user's head.

As discussed above, the earmuffs 10 can be passive, which does not require any electronic aid to provide hearing protection. If additional protection is desired, however, the earmuffs 10 can further include electronic sound dampening devices or assemblies 34 mounted to each of the cups 12. Each sound dampening assembly 34 includes a microphone 36 positioned on an outer surface 38 of the cup 12. The microphone 36 picks up ambient sounds from around the user and transmits the ambient sounds to a sound compression or suppression circuit mounted inside the cup 12 that filters out or suppresses sounds above a predetermined decibel level. Sounds lower than the set level are then transmitted to earphones inside the earpads 16 so that a user of the earmuffs 10 can hear non-damaging sounds in the environment, such as people talking nearby. The sound circuit can be adjusted by a volume switch device or knob 40 mounted to the cup 12 and electrically coupled to the dampening device 34. The volume knob 40 can include an off position and be rotated to turn the dampening device 34 on and sequentially increase the volume of the device 34 with additional rotation thereof. As shown, each of the cups 12 includes the microphone 36 and volume knob 40; however, the earmuffs 10 could instead include only one of each to control the operation of both cups 12. In order to power the sound dampening assembly 34, each cup 12 can include a power source compartment 42 therein. The power source compartment 42 can be configured to receive replaceable batteries 44, such as AAA, AA, coin-cell, 9 volt, or the like, therein. Alternatively, the power source compartment 42 can be sized and configured to receive one or more rechargeable batteries 44 therein. Electrical connections 45, such as wires, circuit boards, traces, or the like, extend between and electrically couple the microphone 36, volume knob 40, and power source 44. In the form utilizing the rechargeable battery, the cup 12 can further have a port 46 mounted within a port opening 48 of the cup 12 that is electrically coupled 45 to the other components of the sound dampening assembly 34. The port 46 can receive any suitable plug, such as a USB, mini-USB, or the like, to connect the rechargeable battery to a power outlet and provide recharging power thereto. Moreover, the circuitry of the sound dampening device 34 can include ambient sound magnification and auto shut-off features, such as when a predetermined amount of time has passed, to conserve battery life.

Turning now to lighting features for the earmuffs 10 as shown in FIGS. 1A-3, one or more light modules 100 are configured to mount to the cups 12 of the earmuffs 10 to project light forwardly thereof. The light module 100 includes a housing 102 having a light assembly 104 received therein. The housing 102 is configured to mount to the rigid backing 14 of the cups 12 to securely hold the light module 100 thereto. In one form, the housing 102 can include upper and lower through bores 106 and 108 sized and configured to receive fasteners 110 such as screws or other attachment structure therethrough. Further, the cup 12 includes upper and lower threaded bores 112 and 114 therein configured to align with the through bores 106 and 108 in the light module 100 and sized to threadingly receive the screws 110 therein. If desired, the screws 110 can include an outwardly projecting head 116 that can easily be grasped to remove the light module 100 from the earmuffs 10, such as by a user wearing gloves or the like. As shown, the housing 102 only includes one each of the upper and lower through bores 106 and 108; however, other configurations can be utilized, such as through bores at the corners of the housing 102, forward and rearward through bores, or the like.

The light assembly 104 includes one or more light sources 120, which are preferably LEDs, a switch device 122 configured to shift the light sources 120 between on and off configurations, and a power source 124. In the illustrated form, the light sources 120 are mounted to the housing 102 to project light forwardly from a forward surface 126 thereof. Specifically, the housing forward surface 126 includes one or more openings 128 therein corresponding to the number of light sources 120 and the light sources 120 are mounted at least partially within the housing 102 to project light forwardly from the openings 128. Moreover, in order to block incident light, each light source 120 can be mounted within a bezel 132 of or mounted to the housing 102 and be oriented to project light forwardly from the forward surface 126 thereof. The bezel 132 includes an annular cavity 134 therein sized to receive the light source 120. As shown, there are two light sources 120 mounted to the housing 102 in a vertically stacked configuration; however, other configurations can also be utilized, such as configurations using less or more light sources, light sources being mounted laterally adjacent to one another, light source mounted within bezels on an outer surface 136 of the housing 102, or the like.

The housing 102 further includes a power source compartment 138 sized to receive the light assembly power source 124. The power source compartment 138 can be configured to receive replaceable batteries, such as AAA, AA, coin-cell, 9 volt, or the like, therein. Alternatively, the power source compartment 138 can be sized and configured to receive one or more rechargeable batteries therein. In the form utilizing the rechargeable battery, the light assembly 104 can further include a port 140 mounted within a port opening 142 of the housing 102 and electrically coupled to the other electrical components of the lighting assembly 104. The port 140 can be configured to receive any suitable plug, such as a USB, mini-USB, or the like, to connect the rechargeable battery 124 to a power outlet and provide recharging power thereto. For the form using the replaceable batteries 124, the power source compartment 138 can further include a cover 144 that can be removable from the housing 102 or otherwise movable between open and closed configurations, such as by sliding off of or pivoting away from the power source compartment 138.

Figure 1B:
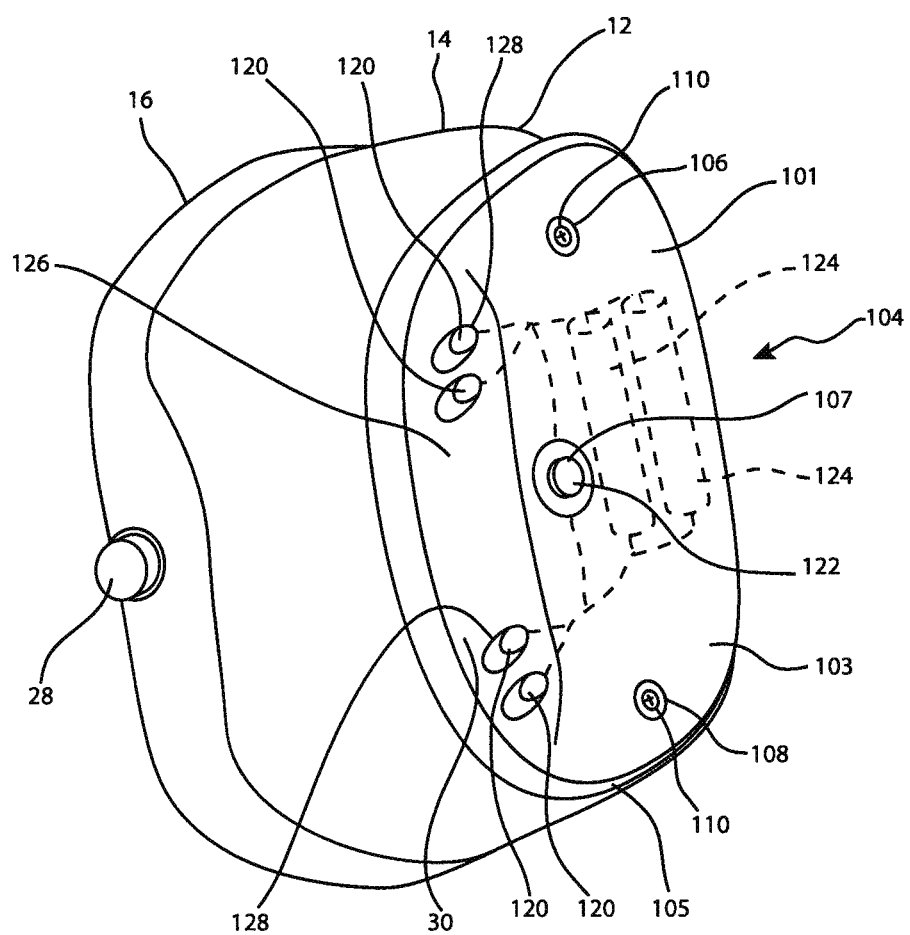
FIG. 1B is a perspective view of lighted headgear showing ear covering assemblies connected by a headband and alternative light modules mounted to the ear covering assemblies to project light forwardly thereof.

Another form of earmuffs 10 having a light module 101 mounted thereto is shown in FIG. 1B. As with the above form, the light module 101 is configured to mount to the cups 12 of the earmuffs 10 to project light forwardly thereof and includes a housing 103 with the light assembly received therein. Accordingly, only the differences will be discussed hereinafter. In this form, the housing is sized and configured to provide a smooth transition from the cup 12 to the module 101 so that the appearance of the cup 12 is maintained. Pursuit to this, a periphery of the module 101 is sized to be flush with or slightly smaller than a sidewall of the cup 12. Additionally, the module 101 can have a domed shape so that the module 101 has the appearance of the outer surface of the cup 12.

As shown in FIG. 1B, the module 101 includes four light sources mounted vertically along the housing front surface. In the illustrated form, the light sources are mounted in upper and lower pairs spaced vertically from one another. Additionally, the light module 101 has an open back so that the batteries 124 can be accessed therethrough. Thus, a removable battery compartment cover is unnecessary. Instead, user can simply unscrew the fasteners 110 to remove the module 101 from the cup 12. In order to protect the interior of the light module 101 from water and debris, a seal member 105 can be disposed between the housing 103 and the cup 12 when the housing 103 is mounted thereto and a flexible switch cover member 107 can be disposed over an actuator of the switch device 122. One or both of the cups 12 can have one of the light modules 101 attached thereto. Additionally, the cup of this form can have the pivot connections 28 generally centrally along a vertical axis at the forward and rearward surfaces 30, 32 of the cups 12.

Figure 3:
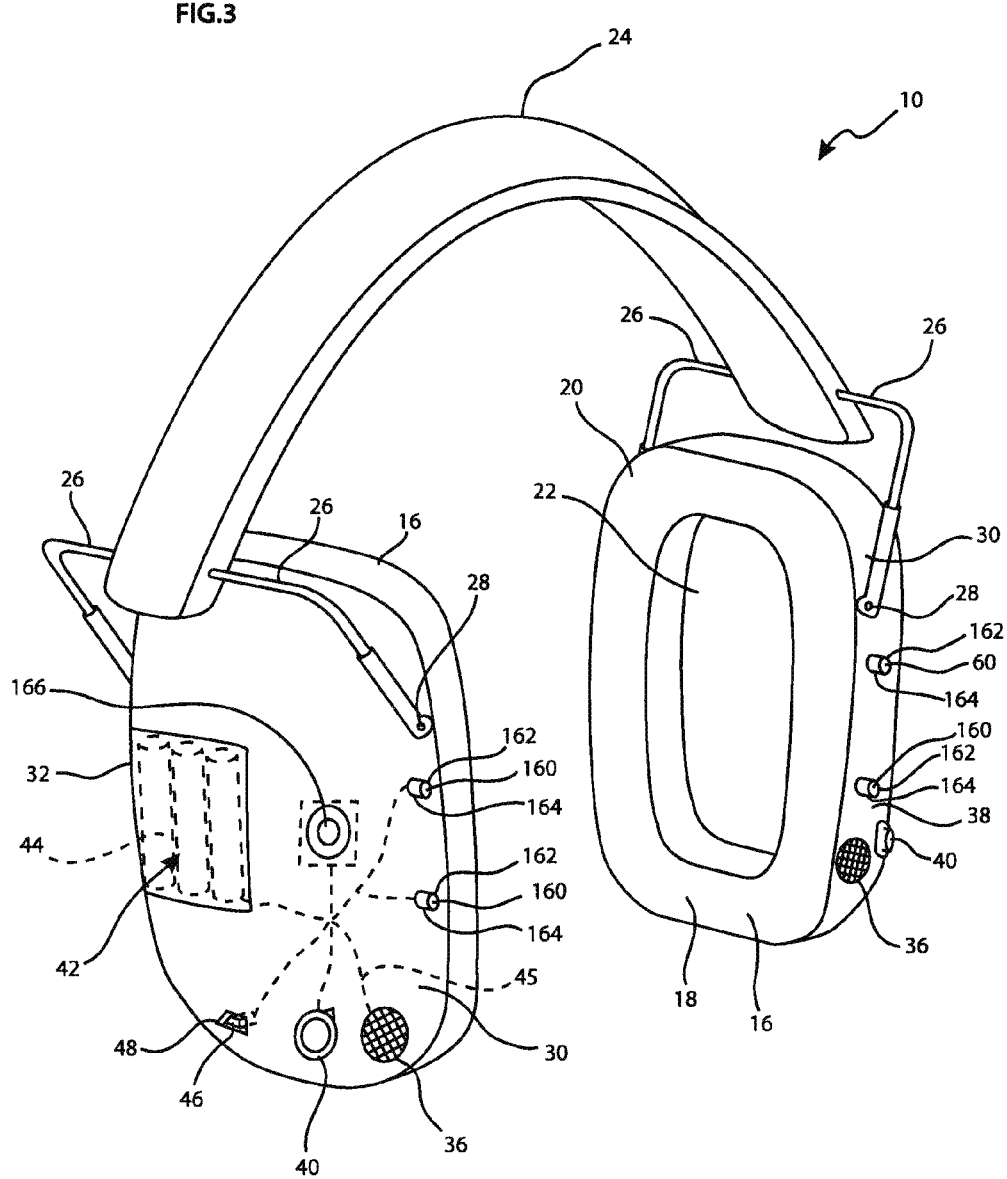
FIG. 3 is a perspective view of lighted headgear showing lighted ear covering assemblies connected by a headband.

Alternatively, as shown in FIGS. 2 and 3, the earmuffs 10 can utilize the power source from the sound dampening assembly to power the light source. In the example of FIG. 2, the light module 100 including the switch device 122 received therein can be mounted to the cup 12 of the earmuffs 10 in a manner similar to that discussed above, but the light module 100 can further include a plug 150 configured to be inserted through an opening 152 in the rigid backing 14 and into a socket 154 electrically coupled to the sound dampening assembly 34 and the power source 44 thereof by the electrical connections 45. As such, the power source 44 of the sound dampening assembly can be utilized to power the light sources 120 of the light module 100 and the light module 100 need not include the space and weight needed for housing a power source. This allows the light module 100 to have a smaller profile and lighter weight.

In another example, as shown in FIG. 3, light sources 160 can be mounted directly to the cup 12 and electrically coupled to the other components of the sound dampening assembly 34 by the electrical connections 45. As such, the cup 12 can include openings 162 in the forward surface thereof through which the light sources 160 can project light forwardly of the earmuffs 10. Further, if desired, the light sources 160 can be mounted within bezels 164 of the cup 12, similar to that discussed above. The volume knob 40 can be utilized to shift the light sources 160 between on and off configurations, as discussed above. Alternatively, a separate switch device 166, configured similar to the switch device 122, can be mounted to the cup 12 and electrically coupled to the light sources 160, as well as other components of the assembly 34, if desired.

Any of the light sources 120 or 160 and their orientation structure such as the bezels 132 or 164, housings 100, or cups 12 can be canted to direct light to a convenient area for a user. For example, one or both of the light sources 120 or 160 can be canted inwardly to illuminate an area relatively closer to a user, such as within arms reach. Alternatively, or in addition thereto, one or both of the light sources 120 or 160 can be canted downwardly to illuminate an area below horizontal from the lighted earwear. As such, the light sources and their oriented structure can take any of the forms described in U.S. Ser. No. 12/895,456, filed Sep. 30, 2010 and PCT/US12/71480, which are hereby incorporated by reference herein in their entirety.

It will be understood that various changes in the details, materials, and arrangements of the parts and components that have been described and illustrated in order to explain the nature of the lighted components as described herein may be made by those skilled in the art within the principle and scope of this disclosure.

The invention claimed is:

1. Lighted headgear comprising:
   a connecting band portion having opposite end portions;
   ear assemblies mounted to the end portions of the connecting band portion;
   ear engagement portions of the ear assemblies configured to engage the ears of a wearer;
   a self-contained light module mounted to one of the ear assemblies;
   a housing of the light module having a power source compartment and an open back providing access to the power source compartment, the housing configured to mount to the one of the ear assemblies such that the open back thereof is covered by the one of the ear assemblies; and
   an electronic assembly of the light module received within the housing thereof, the electronic assembly including a light source mounted to project light forwardly of the ear assembly, a power source configured to provide power to the light source with the open back of the housing allowing for replacement of the power source, and a switch device electrically coupled to the power source and the light source to selectively switch the light source between on and off states.

2. The lighted headgear of claim 1, wherein the light module further includes a seal member mounted to the housing, the seal member configured to be disposed between the one of the ear assemblies and the housing when the housing is mounted to the one of the ear assemblies to thereby seal the open back of the housing.

3. The lighted headgear of claim 1, wherein the light module housing includes a mounting opening in a forward facing surface thereof, and the light source is mounted in the mounting opening to project light forwardly of the light module.

4. The lighted headgear of claim 1, wherein the housing and the ear engagement portion include aligned bores to receive fasteners therein to mount the housing to the ear engagement portion.

5. The lighted headgear of claim 1, wherein the electronic assembly includes a plurality of light sources.

6. The lighted headgear of claim 5, wherein the plurality of light sources are mounted in a vertically stacked orientation.

7. The lighted headgear of claim 1, wherein the switch device is a pushbutton switch device with a switch base and a switch actuator; and the pushbutton switch device is disposed partially within the light module housing so that the switch actuator is accessible at an exterior surface thereof.

8. The lighted headgear of claim 1, wherein the ear engagement portions of the ear assemblies comprise cups that are configured to encompass the ears of a wearer in order to provide hearing protection therefor.

9. The lighted headgear of claim 8, wherein the cups each include a sound dampening assembly to actively filter out or suppress external noises above a predetermined decibel level.

10. The lighted headgear of claim 1, wherein the ear assemblies are pivotably connected to the end portions of the connecting band portion for conforming to the head of a wearer.

11. The lighted headgear of claim 10, wherein the end portions of the connecting band portion include generally u-shaped arm members, the ear assemblies include pivot connections, and the arm members couple to the pivot connections to pivotably mount the ear assemblies to the connecting band portion.

12. The lighted headgear of claim 1, wherein the power source is a rechargeable power source; and the electronic assembly includes a port connected to the rechargeable power source and configured to receive recharging power from an external source.

13. A cup assembly for hearing protection, the cup assembly comprising:
   a substantially rigid cup-shaped member including edges defining an opening to an interior thereof;
   an annular earpad portion mounted to the cup-shaped member configured to generally extend about the opening and the ear of a wearer;
   a spanning earpad portion disposed within the cup-shaped member interior to cover the ear of a wearer;
   a light module including a housing having a domed configuration and edges defining an opening to an interior thereof, the light module mounted to the cup-shaped member such that the opening is oriented towards the cup-shaped member; and
   a light assembly disposed within the light module housing interior and including a light source mounted to project light forwardly of the cup-shaped member, a power source configured to provide power to the light source and accessible through the opening in the housing for replacement thereof, and a switch device configured to selectively energize the light source.

14. The cup assembly of claim 13, further comprising a seal member disposed between the housing and the cup-shaped member.

15. The cup assembly of claim 13, wherein the light module housing includes a mounting opening in a forward surface thereof, and the light source is mounted in the mounting opening to project light forwardly of the light module.

16. The cup assembly of claim 13, wherein the light source comprises a plurality of light sources.

17. The cup assembly of claim 13, further comprising a sound dampening assembly mounted to the cup-shaped member, the sound dampening assembly including a power source, a microphone, and a volume adjustment device.

18. The cup assembly of claim 13, wherein the power source is a rechargeable power source, and the light assembly further includes a port coupled to the rechargeable power source configured to receive recharging power from an external power source.

19. The cup assembly of claim 13, wherein the cup-shaped member includes a pivot member configured to pivotably couple the cup-shaped member to a band.

20. The lighted headgear of claim 1, wherein the ear engagement portions comprise cups configured to be disposed over the ears of a wearer, each of the cups including a substantially rigid backing member and an ear pad mounted to the backing member.

21. The lighted headgear of claim 20, wherein the housing is sized and configured to provide a smooth transition from the substantially rigid backing member to the light module so that the appearance of the ear assemblies is maintained.

22. The lighted headgear of claim 13, wherein the housing is sized such that a periphery thereof is flush with or slightly smaller than a sidewall of the cup-shaped member.

23. The lighted headgear of claim 22, wherein an outer surface of the cup-shaped member has a rounded configuration such that the domed configuration of the housing provides the appearance of the outer surface of the cup-shaped member.

24. Lighted headgear comprising:
a connecting band portion having opposite end portions;
ear assemblies mounted to the end portions of the connecting band portion;
substantially rigid cup-shaped members of the ear assemblies;
a self-contained light module mounted to one of the cup-shaped members;
a housing of the light module having a footprint and curved configuration so that the light module has the appearance of an outer surface of the one of the cup-shaped members; and
a light assembly disposed within the housing and including a light source mounted to project light forwardly of the one of the cup-shaped members, a power source configured to provide power to the light source, and a switch device configured to selectively energize the light source.

25. The lighted headgear of claim 24, wherein the footprint of the housing is sized such that a periphery of the housing is flush with or slightly smaller than a sidewall of the one of the cup-shaped members.

26. The lighted headgear of claim 24, wherein the cup-shaped member has a generally oval cross-section taken along a plane generally parallel to an ear of a user and the footprint of the housing is a smaller, generally complementary oval.

27. The lighted headgear of claim 24, wherein the light module includes edges defining an opening to an interior thereof; the light module is configured to mount to the one of the cup-shaped members such that the opening is oriented towards the one of the cup-shaped members; and the power source of the light assembly is accessible through the opening in the housing when the housing is removed from the one of the cup-shaped members.

28. The lighted headgear of claim 24, further comprising a seal member disposed between the housing and the cup-shaped member.

29. The lighted headgear of claim 28, wherein the seal member projects outwardly of the footprint of the housing when the light module and seal member are mounted to the one of the cup-shaped members.

* * * * *